United States Patent [19]

Noiles

[11] 4,060,089
[45] Nov. 29, 1977

[54] SURGICAL FASTENING METHOD AND DEVICE THEREFOR

[75] Inventor: Douglas G. Noiles, New Canaan, Conn.

[73] Assignee: United States Surgical Corporation, Baltimore, Md.

[21] Appl. No.: 609,949

[22] Filed: Sept. 3, 1975

[51] Int. Cl.$^2$ .................. A61B 17/12; A61B 17/08
[52] U.S. Cl. .............................. 128/325; 128/337; 128/334 C; 227/60
[58] Field of Search ............... 128/325, 334 R, 334 C, 128/335, 335.5, 337, 346, 329, 330; 11/1 MB; 227/60

[56] References Cited

U.S. PATENT DOCUMENTS

| 719,475 | 2/1903 | Knight | 227/60 |
|---|---|---|---|
| 3,166,072 | 1/1965 | Sullivan | 128/334 C |
| 3,500,829 | 3/1970 | Abramowitz | 128/329 R |
| 3,641,804 | 2/1972 | Oudenhoven | 128/330 |
| 3,744,495 | 7/1973 | Johnson | 128/337 |
| 3,879,783 | 4/1975 | Giulie | 11/1 MB |

FOREIGN PATENT DOCUMENTS

| 972,731 | 10/1964 | United Kingdom | 128/346 |
|---|---|---|---|
| 392,802 | 5/1933 | United Kingdom | 128/325 |

Primary Examiner—Stephen C. Pellegrino
Attorney, Agent, or Firm—Fleit & Jacobson

[57] ABSTRACT

A method for joining soft body tissues and a device for practicing the method which includes a retainer strip formed of a material which in time is absorbed by the body and which is provided with a plurality of longitudinally spaced openings and a fastener strip also formed of a material which is similarly absorbed and which is provided with a plurality of longitudinally spaced prongs each having a barbed end portion and an axial passage. Both the retainer strip and fastener strip are preferably formed of biologically absorbable plastic material for gradual absorption by the body and are movable together so that the prongs are inserted through the tissue to be joined and through the retainer strip openings with the tissue secured between the strips. The strips are movable together by means of a rigid anvil member engageable with the retainer strip and a rigid pusher member engageable with the fastener strip. A plurality of spaced pins is provided on the pusher member for insertion into respective prong passages to maintain the prongs rigid during the joining procedure, separation of the fastened strips is prevented by the barbs on the prongs.

11 Claims, 5 Drawing Figures

SURGICAL FASTENING METHOD AND DEVICE THEREFOR

BACKGROUND OF THE INVENTION

One of the most common surgical procedures in the medical field is the suturing of body tissues such as that of the stomach, intestines, other organs and the like. Efforts to reduce time required to perform surgical procedures and to improve the techniques of surgically joining tissues have resulted in the increased use of such devices as surgical staples, hemostatic clips and the like which may be quickly applied in a precise manner. Such devices have been designed to be used with actuating instruments by means of which the device, such as a surgical staple, is applied during a tissue joining procedure precisely and with a minimum of effort. Present day devices have produced excellent results in clinical use and have reduced the time required for many surgical procedures. However, in some cases it may be highly desirable that the fastening devices be eventually absorbed by the body for physiological or other medical reasons.

This invention provides a new and novel device for joining body tissues which device may be fabricated in a variety of lengths and sizes and which utilizes biologically absorbable material, the components of which may be applied in a precise and rapid manner by a mechanically actuated device.

A still further object of the invention is to provide a new and novel method for joining tissues precisely and rapidly.

Still another object of this invention is to provide a new and novel surgical fastener of biodegradable material.

Another object of this invention is to provide a new and novel method for using a surgical fastener of biodegradable material for joining tissues securely and rapidly.

This invention includes an elongated retainer strip of biologically absorbable material having a plurality of longitudinally spaced openings. Such retainer strip is positioned on one side of the tissues to be joined. The fastener strip is provided with a plurality of spaced parallel prongs, each prong arranged to be inserted in one of the retainer strip openings with the prongs extending through the retainer strip to the extent necessary for securing the tissues between the strips. Means are provided on the prongs for retaining the prongs in the openings in the retainer strip. Each of the prongs of the fastener strip is provided with an axial central passage.

An elongated rigid anvil aligns and supports the retainer strip during the joining procedure. Similarly an elongated rigid pusher member aligns and supports the fastener strip. The pusher member is provided with a plurality of spaced pointed pins which engage the fastener strip with the pins within the central passages of the prongs to impart rigidity to the prongs during the joining procedure. The pointed pins of the pusher member extend through the ends of the prongs of the fastener strip in order to facilitate the passage of the prongs through the tissues to be fastened. The use of a suitable actuating instrument for moving the pusher member with the fastener strip toward the anvil member with the retainer strip permits driving the prongs through the tissues to be joined and into the appropriate holes in the retainer strip. The barbs on the prongs pass through the retainer strip creating a locked assembly with the tissue secured between the strips.

DESCRIPTION OF THE PREFERRED EMBODIMENTS

Figure 5:
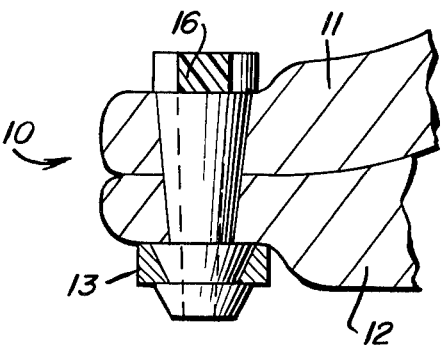
FIG. 5 is a view similiar to FIG. 4 showing the device of the invention in the applied position with the associated parts removed.

Referring now to the drawings, there is shown in FIG. 5 a fastening device constructed in accordance with the invention and designated generally by the numeral 10. The fastening device 10 is shown joining together soft body tissue portions 11, 12.

The fastening device 10 includes an elongated retainer strip 13 of biologically degradable or body absorbable material which is positioned on one side of the tissue to be joined, such as the tissue portion 12. The retainer strip 13 may be of any suitable length in accordance with the length of the joining procedure to be accomplished. For instance, although in the illustrated embodiment, the retainer strip 13 is provided with a plurality of longitudinally spaced openings 14 extending transversely therethrough, it is within the scope of the invention to provide only one such opening 14, the strip 13 being shortened accordingly.

Figure 1:
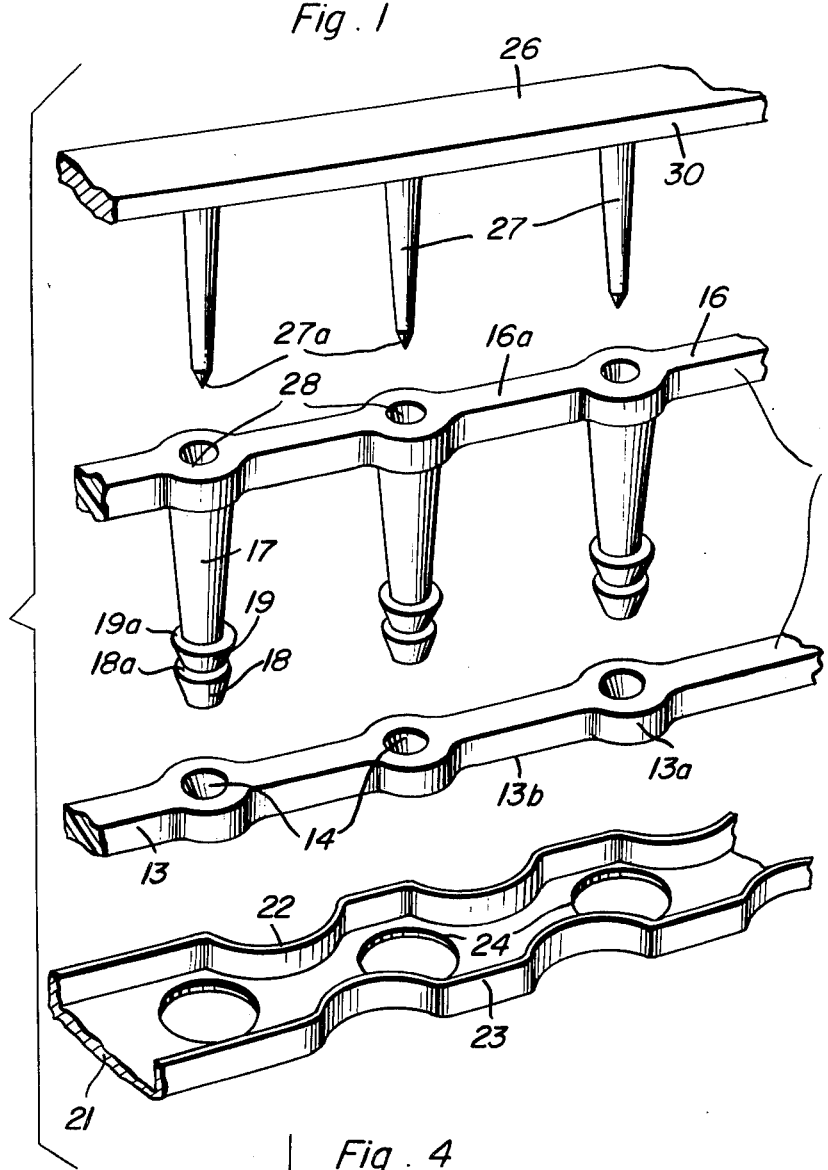
FIG. 1 is an exploded view of the surgical fastening device of the invention together with the associated parts used in conjunction therewith.

As shown in FIG. 1, the openings 14 are preferably of conical shape and the strip 13 may be provided with enlarged portions 13a adjacent the openings 14 to create uniform strength over the length of the strip.

The fastening device 10 also includes an elongated fastener strip 16 similarly of biodegradable or absorbable resinous material having a length substantially the same as that of the retainer strip 13. The fastener strip 16 is provided with a plurality of longitudinally spaced prongs 17 preferably formed integrally therewith, the spacing of which corresponds to the spacing of the openings 14 in the retainer strip 13. It should be understood that in the shortened version of the strip 13 wherein only a single opening 14 is provided, only a single prong 17 is provided on the fastener strip 16.

The fastener strip 16 and retainer strip 13 are arranged to be moved together into securing engagement with the tissue layers 11, 12 disposed therebetween, the pin points 27a and prongs 17 piercing the joined tissues and inserted in the openings 14 during the fastening procedure to the extent determined by the thickness of the tissues between the strips. Means are provided on the prongs 17 for retaining the prongs in the openings 14 at the extent inserted and, in the illustrated embodiment, such retaining means include one or more barbs 18, 19 on the end of each of the prongs 17. As shown best in FIG. 4, the upper surfaces 18a, 19a of the barbs 18, 19 are arranged for selective engagement with the underside 13b of the strip 13 to prevent withdrawal of the prongs 17 from the openings 14.

Figure 3:
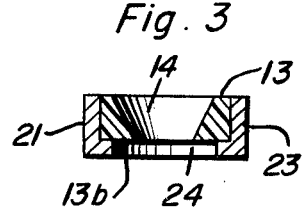
FIG. 3 is an assembled view of another portion of the invention of FIG. 1.

In order to position the strips 13, 16 in proper alignment and for proper mating during the tissue joining procedure, as well as for moving the strip together into engagement, an elongated anvil member 21 of rigid material such as metal or the like is provided for supporting the retainer strip 13. As best shown in FIG. 3, the metal anvil member 21 is arranged to be positioned in relationship with the retainer strip 13 in engagement with the underside 13b and may be provided with longitudinally extending shaped side flanges 22 and 23 as shown in FIG. 1 for preventing longitudinal and lateral displacement of the strip 13 on the anvil member 21. The anvil member 21 is also preferably provided with a plurality of longitudinally spaced openings 24, the spacing of which corresponds to the spacing of the openings 14 in the retainer strip 13. The openings 24 are arranged to accommodate the end portion of the prongs 17 projecting beyond the underside 13b of the strip 13 against which the anvil 21 is positioned.

In order to align and support the fastener strip 16 for the joining procedure, a pusher member 30 is provided, as shown best in FIG. 1, which is preferably in the shape of an elongated bar 26 of rigid material such as metal or the like which is arranged to engage the upper surface 16a of the fastener strip 16. The pusher member 30 is provided with a plurality of longitudinally spaced pins 27, the spacing of which corresponds to the spacing of the prongs 17.

Figure 2:
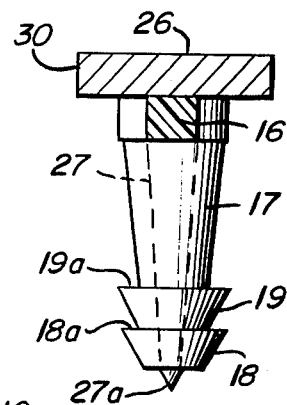
FIG. 2 is an assembled view of a portion of the invention of FIG. 1.

The pins 27 are arranged to be inserted into corresponding axially extending central passages 28 extending through the prongs 17 of the fastener strip 16 as shown in FIG. 2. In order that the prongs 17 easily pierce the tissue to be sutured during the suturing operation, the outer ends of the pins 27 are provided with sharpened points 27a. The length of the pins 27 and the prongs 17 is selected so that in the assembled relationship of FIG. 2, the bar 26 will bear on strip 16 and serve to take up the thrust.

In carrying out a joining procedure the fastener strip 16 is positioned on the pusher member 30 with the pins 27 extending within the passages 28 so as to maintain the prongs 17 in a rigid condition during the joining procedure. As can be understood, the plastic material from which the strip 16 and prong 17 are formed may not sufficiently rigid to maintain the prongs 17 of themselves in an aligned position with the openings 14 in the strip 13 during the piercing of the tissue to be joined and the securing of the tissue between the strips 13, 16. However, with the metal pins 27 within the central passages 28 of the prongs 17 and with the points 27a of pins 27 extending through the prongs 17 to provide sharp penetrating points, the prongs 17 are sufficiently inflexible so that they are maintained in alignment with the strip openings 14. Piercing of the tissue is facilitated by the sharp points 27a on the pins 27.

With the anvil member 21 and retainer strip 13 assembled, as shown in FIG. 3, on one side of the tissue layer 12 and the fastener strip 16 and pusher member 30 assembled as shown in FIG. 2 on the other side of the tissue to be joined such as tissue layer 11, the strips 13, 16 are moved together. The fastener strip 16 is moved toward the retainer strip 13 with the points 27a and prongs 17 piercing the tissue layers 11, 12. The barb 18 on each of the prongs 17 then enters its associated opening 14 in strip 13, and if so determined by the thickness of the tissue to be joined the prongs 17 move through the openings 14 only to the extent wherein locking engagement results between the barbed surface 18a and the surface 13b of the retainer strip 13 as permitted by the anvil member openings 24. If the tissue to be joined is of a thickness such that further movement of the prongs 17 in the openings 14 is required, the barbs 19 move through the openings 14 whereupon the surfaces 19a of the barbs 19 engage the surface 13b of the retainer strip 13.

Figure 4:
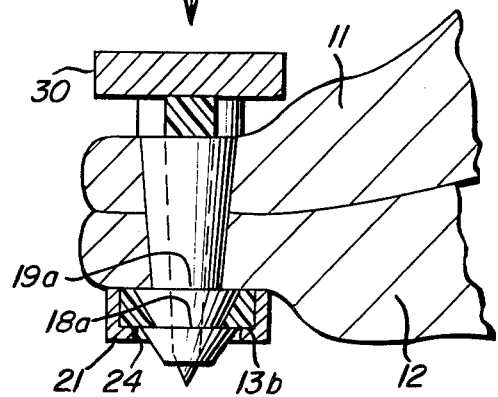
FIG. 4 is a perspective view showing the invention in the applied position together with the associated parts.

The two strips 13, 16 are therefore now inerconnected in an assembled relationship with the tissues secured therebetween as shown in FIG. 4 completing the joining procedure. At that time, the anvil member 21 and pusher member 30 are removed leaving the strips 13, 16 in the applied position with the tissues 11, 12 secured as shown best in FIG. 5.

Materials that are suitable for use as absorbable or biodegradable fasteners include cat gut (collagen derived from sheep intestinal submucosa), polyglycolic acid, polylactic acid, copolymer blends of polyglycolic and polylactic acid, reconstituted collagen, erodible metallic alloys, polyesters, polyamino acids such as casein, albumin and the like, polyhydric alcohol polymers such as polyvinyl alcohol, cellulose glycolic acid ethers and esters of alpha-cyanacrylic, acid such as methyl alpha-cyanoacrylate. Polyglycolic acid is disclosed in U.S. Pat. 3,463,158; 3,739,773 and 3,772,420. Suitable polylactic acids are disclosed in U.S. Pat. Nos. 3,636,956. Examples of absorbable polyesters are shown in U.S. Pat. Nos. 3,225,766 and 3,883,901. Absorbable cellulose glycolic acid ethers are shown in U.S. Pat. No. 2,764,159. Examples of suitable esters of alpha-cyanoacrylic acid are found in U.S. Pat. Nos. 3,527,841, 3,564,078 and 3,759,264.

What is claimed is:

1. A surgical fastening device comprising, in combination, a retaining member of absorbable material having an opening therein and arranged to be positioned on one side of body tissue, a fastener member of absorbable material having a prong thereon arranged to be inserted through the tissue disposed between said members and into said retainer member opening to the extent that the tissue is secured between said fastener member and said retainer member, means on said prong for retaining said prong in said retainer member, and means for maintaining said prong in a rigid condition during a tissue joining procedure as the prong is inserted through the tissue into said retainer member opening to secure the tissue.

2. A surgical fastening device in accordance with claim 1, wherein said means for maintaining said prong in a rigid condition includes a central passage formed in said prong and a pin arranged to be inserted into said central passage of said prong to maintain said prong in a rigid condition during said tissue joining procedure.

3. A surgical fastening device in accordance with claim 2, wherein said pin has a sharp end portion and said pin is of sufficient length to extend completely through said central passage in said prong so that said sharp end portion of said pin extends outwardly from the end of said prong thereby permitting said prong to pierce said tissue.

4. A surgical fastening device for joining soft body tissues, comprising, in combination, an elongated retainer strip of absorbable material having a plurality of longitudinally spaced openings and arranged to be positioned on one side of the tissues to be joined, and elongated fastener strip of absorbable material having a plurality of prongs thereon arranged in longitudinally spaced, parallel relationship corresponding to the spacing of said retainer strip openings, each of said prongs arranged to be inserted through the tissues to be joined disposed between said strips and into one of said retainer strip openings to an extent such that the tissues are secured between said fastener strip and said retainer strip, means on said prongs for retaining said prongs in said openings to the extent inserted, an elongated rigid anvil member for supporting said retainer strip during the tissue joining procedure, a rigid pusher member engageable with said fastener strip during said tissue joining procedure whereby relative movement between said anvil member and said pusher member permits said fastener strip and said retainer strip to be moved together into fastening engagement with said tissues.

5. A surgical fastening device in accordance with claim 4, including means on said pusher member for maintaining said prongs in a rigid condition during said tissue joining procedure.

6. A surgical fastening device in accordance with claim 5, wherein said means for maintaining said prongs in a rigid condition include a central passage of each of said prongs and a plurality of pins on said pusher member spaced correspondingly to the spacing of said prongs, each of said pins being arranged to be inserted into the central passage of the corresponding prong to maintain said prongs in a rigid condition during said tissue joining procedure.

7. A surgical fastening device in accordance with claim 6 wherein each of said pins is provided with a sharp outer end portion, said sharp end portion being arranged to extend outwardly from the outer end of said prong when said pin is disposed within said central passage in said prong thereby permitting said prongs to pierce said tissues to be joined during the tissue joining procedure.

8. A surgical fastening device in accordance with claim 4, including a plurality of longitudinally spaced openings in said anvil member for accommodating the outer end portions of said prongs extending through said openings in said anvil member.

9. A method of surgically joining soft body tissues comprising the steps of supporting one side of the tissues to be joined with a structure of absorbable material, positioning a structure of absorbable material on the other side of said tissues, moving said structures on opposite sides of said tissues to be joined together to pierce the tissues and to secure the tissues therebetween, maintaining said structures in a rigid condition during a tissue joining procedure as the tissues are pierced and secured therebetween, and maintaining said structures with said tissues secured therebetween while permitting said structures to be gradually absorbed.

10. A method of surgically joining soft body tissues comprising the steps of positioning a two component structure of absorbable material having interconnecting means thereon with one component on each side of the tissues to be joined, moving the two components of said structure together into interconnected engagement with said tissues pierced and secured thereby, maintaining said two component structure in a rigid condition during a tissue joining procedure as said two components are moved together into interconnected engagement, and permitting said structure to be absorbed within the body.

11. A surgical fastening device comprising, in combination, a retaining member of absorbable material having an opening therein and arranged to be positioned on one side of the tissue, a fastener member of absorbable material having a prong thereon arranged to be inserted through tissue disposed between said members and into said retainer member opening, said prong having a central passage extending longitudinally through said prong, barbs on said prong for retaining said prong in said retainer member, a pusher member having a pin arranged to be inserted into said central passage of said prong to maintain said prong in a rigid condition during tissue joining procedure as said prong is inserted through the tissue and into said retainer member opening, and an anvil member adapted to maintain said retaining member in a rigid condition during said tissue joining procedure.

* * * * *